(12) United States Patent
Jacoby

(10) Patent No.: US 7,091,151 B2
(45) Date of Patent: Aug. 15, 2006

(54) CATALYTIC SYSTEM FOR ALDOL REACTIONS

(75) Inventor: Denis Jacoby, Nyon (CH)

(73) Assignee: Firmenich SA, Geneva (CH)

(*) Notice: Subject to any disclaimer, the term of this patent is extended or adjusted under 35 U.S.C. 154(b) by 26 days.

(21) Appl. No.: 11/001,114

(22) Filed: Dec. 2, 2004

(65) Prior Publication Data
US 2005/0080297 A1    Apr. 14, 2005

Related U.S. Application Data

(60) Division of application No. 10/688,297, filed on Oct. 17, 2003, now Pat. No. 6,838,575, which is a continuation of application No. PCT/IB02/01839, filed on May 21, 2002.

(30) Foreign Application Priority Data
May 22, 2001  (WO) .................. PCT/IB01/00902

(51) Int. Cl.
   *B01J 31/00*   (2006.01)
   *C07F 7/00*    (2006.01)
(52) U.S. Cl. .................... 502/171; 556/51; 556/54
(58) Field of Classification Search ............ 502/171; 556/51, 54
   See application file for complete search history.

(56) References Cited

U.S. PATENT DOCUMENTS 4,367,321 A * 1/1983 Bachl et al. ............ 526/124.8
4,525,554 A * 6/1985 Tanaka et al. ........... 526/124.8
6,617,278 B1 * 9/2003 Jin et al. .................. 502/134

FOREIGN PATENT DOCUMENTS

EP    0 676 393 A1    10/1995

OTHER PUBLICATIONS

Ayyar et al., "Synthesis of δ-Damascone [trans-1-(2,6,6-Trimethylcyclohex-3-enyl)but-2-en-1-one] and β-Damascenone [trans-1-(2,6,6-Trimethylcyclohexa-1,3-dienyl)but-2-en-1-one]," Perkin Trans. 1, vol. 17, pp. 1727-1736 (1975).
Ishimaru et al., "Novel Cationic Titanium (IV) Lewis Acids and Their Use in Asymmetric Aldol Reactions," Tetrahedron 54, pp. 727-734 (1998).
Vedejs et al., "A Synthesis of the $C_6,C_{11}$-Dideoxyanthracyclinone Skeleton via Hassall Cyclization and Oxidative Desilylation," J. Org. Chem., vol. 53, No. 8, pp. 1593-1599 (1988).

* cited by examiner

Primary Examiner—Porfirio Nazario-Gonzalez
(74) Attorney, Agent, or Firm—Winston & Strawn LLP

(57) ABSTRACT

The invention relates to a catalytic system for use in a process for the preparation, in a single step, of enones by an aldol condensation of a ketone, such as a gem-dimethyl cyclohexylethanone or gem-dimethyl cyclohexenylethanone derivative, with an aldehyde in the presence of a novel catalytic system and a co-ingredient, such as a carboxylic acid anhydride or an anhydrous salt, and without the preformation of an enolate. The catalytic system is a metal complex, such as a $[(Cl)_n(\text{alkoxy})_{4-n}Ti]$ or $[(Cl)_n(\text{alkoxy})_{4-n}Zr]$ complex where n is 1 to 3.

4 Claims, No Drawings

CATALYTIC SYSTEM FOR ALDOL REACTIONS

CROSS-REFERENCE TO RELATED APPLICATIONS

This application is a divisional of U.S. application Ser. No. 10/688,297 filed Oct. 17, 2003 now U.S. Pat. No. 6,838,575, which is a continuation of International application PCT/IB02/01839 filed May 21, 2002, the content of each of which is expressly incorporated herein by reference thereto.

TECHNICAL FIELD

The present invention relates to the field of organic synthesis and more precisely to a single step process for the synthesis of an enone (I):

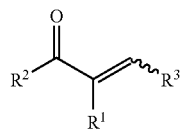

as defined further below.

This process is a catalyzed aldol condensation which does not require the pre-formation of an enolate. The catalytic system is also an embodiment of the invention.

BACKGROUND ART

Cross-aldol condensations involving "low reactivity" ketones, i.e., which need strong reaction conditions to react, and/or "high reactivity" aldehydes, i.e., which undergo self-condensation or polymerization even with soft reaction conditions, are difficult processes as, in general, important amounts of strong bases are required and/or the self-condensation or the polymerization of the aldehyde or of the final enone are frequently observed.

An example of existing process for the cross-aldol condensation between a sterically hindered cyclohexylethanone, a "low reactivity" ketone, and acetaldehyde, a "high reactivity" aldehyde, is the one described in Ayyar et al. *J. Chem. Soc., Prekin Trans.* I, 1975, 17, 1727. However, said method needs the use of a stoichiometric amount of a strong base such as the N-methylanilino magnesium bromide for the formation of an enolate. Strong bases such as an amide anion have the inconvenience of being expensive and difficult to manipulate, therefore a process implying large amounts of base does not represent the best solution for this type of reaction, all the more for an industrial purpose.

SUMMARY OF THE INVENTION

In order to overcome the problems aforementioned, the present invention relates to a new, single step, aldol condensation process, which does not require the pre-formation of an enolate. This process is catalyzed by an original catalytic system including a metal complex and a co-ingredient.

One embodiment of the invention relates to a process for the preparation of a compound of formula (I)

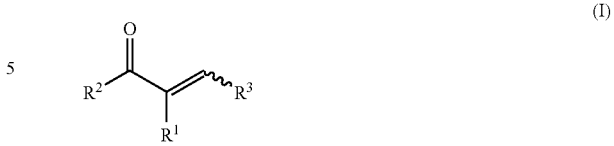

wherein:

the wavy line indicates that the stereochemistry of the C=C double bond is not defined;

$R^1$ represents a hydrogen atom or a methyl group;

$R^2$ represents a methyl or ethyl group or a saturated or unsaturated gem-dimethyl $C_6$ ring, optionally substituted, provided that if $R^1$ is a hydrogen atom $R^2$ is a group having at least two carbon atoms; or said $R^1$ and $R^2$ taken together form a saturated or unsaturated gem-dimethyl $C_6$ ring, optionally substituted, or a saturated or unsaturated $C_{12}$ ring, the ring including the carbon atom of the carbonyl function and the carbon atom to which $R^1$ is bonded; and $R^3$ represents a hydrogen atom, a $C_1$ to $C_4$ linear or branched alkyl or alkenyl group, a linear or branched $C_9$ alkadienyl radical, or a $CH_2R$ group, R being a saturated or unsaturated gem-dimethyl $C_5$ ring that is optionally substituted.

This compound is formed by reacting a starting ketone of formula

wherein $R^1$ and $R^2$ have the same meaning as in formula (I), with an aldehyde of formula

wherein $R^3$ has the same meaning as in formula (I), in the presence of a catalytic system.

Possible substituents of the groups represented by $R^1$, $R^2$, and $R^3$ are methyl, ethyl, methylene or ethylene groups.

DETAILED DESCRIPTION OF THE PREFERRED EMBODIMENTS

In a first preferred embodiment of the invention, the process is aimed at the aldol condensation between a ketone of formula (II) selected from the group consisting of the gem-dimethyl-cyclohexanones, such as 2,2-dimethyl-cyclohexanone, the gem-dimethyl-cyclohexenones, such as 4,4-dimethyl-2-cyclohexen-1-one, and the cyclododecanone, and an aldehyde of formula (III) selected from the group consisting of formaldehyde, acetaldehyde, 2-propenal and 2-butenal, in order to obtain the corresponding enone of formula (I).

In a second preferred embodiment of the invention the ketone of formula (II) is methyl ethyl ketone. Particular example of this embodiment may be the reaction between the campholenic aldehyde, i.e. 2,2,3-trimethyl-3-cyclopentene-1-acetaldehyde, and the methyl ethyl ketone.

In the process according to the second preferred embodiment, the enone of formula (I) is obtained as a mixture of two isomers, i.e., a linear one ($R^1$=H, $R^2$=Et) or a branched one ($R^1$ and $R^2$=Me). In these processes, the main isomer obtained is the branched one, in opposition to the classical aldol reaction involving the formation of enolates.

In a third, more preferred embodiment of the invention, the process is a single step reaction between a ketone of formula (IV) and an aldehyde of formula (V) to obtain an enone of formula (VI), according to Scheme 1.

Scheme 1

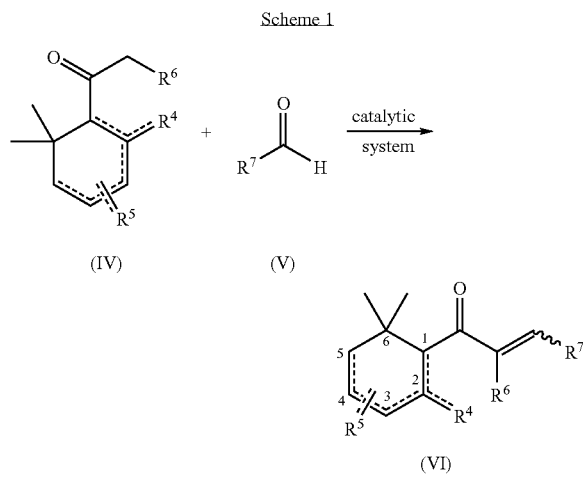

wherein:

the wavy line indicates that the stereochemistry of the C=C double bond is not defined and the dotted lines indicate a single or a double bond;

$R^4$ and $R^5$ represent, simultaneously or independently, a hydrogen atom or a methyl, ethyl methylene or ethylidene group;

$R^6$ represents a hydrogen atom or a methyl group; and $R^7$ represents a hydrogen atom or a $C_1$ to $C_4$ linear or branched alkyl or alkenyl group.

The ketone (IV) may be in the form of a mixture of isomers, i.e. compounds having the same carbon skeleton but with one or two carbon-carbon double bonds in different positions, such as a mixture of at least two of 1-(2,6,6-trimethyl-2-cyclohexen-1-yl)-1-ethanone, 1-(2,2-dimethyl-6-methylene-1-cyclohexyl)-1-ethanone, 1-(2,6,6-trimethyl-1-cyclohexen- 1-yl)-1-ethanone and 1-(2,6,6-trimethyl-3-cyclohexen-1-yl)-1-ethanone, or a mixture of at least two of 1-(2,6,6-trimethyl-1,3-cyclohexadien-1-yl)-1-ethanone, 1-(2,6,6-trimethyl-1,4-cyclohexadien-1-yl)-1-ethanone, 1-(2,6,6-trimethyl-2,4-cyclohexadien- 1-yl)-1-ethanone, 1-(2,2-dimethyl-6-methylene-3-cyclohexen-1-yl)-1-ethanone and 1-(6,6-dimethyl-2-methylene-3-cyclohexen-1-yl)-1-ethanone.

Preferably, $R^4$ represents a methyl or methylene group, $R^5$ represents a hydrogen or a methyl or methylene group, $R^6$ represents a hydrogen atom and $R^7$ represents a methyl group.

A preferred starting aldehyde (V) is acetaldehyde, and a preferred starting ketone (IV) is selected from the group consisting of 1-(2,6,6-trimethyl-1-cyclohexen-1-yl)-1-ethanone, 1-(2,6,6-trimethyl-2-cyclohexen-1-yl)-1-ethanone, 1-(2,6,6-trimethyl-3-cyclohexen-1-yl)- 1-ethanone, 1-(2,2,6-trimethyl-3-cyclohexen-1-yl)-1-ethanone, 1-(2,2-dimethyl-6-methylene-1-cyclohexy 1)-1-ethanone, 1-(2,6,6-trimethyl-1,3-cyclohexadien-1-yl)-1-ethanone, 1-(2,5,6,6-tetramethyl-1-cyclohexyl)- 1-ethanone and 1-(2,2,6-trimethyl-3-methylene-1-cyclohexyl)-1-ethanone.

As mentioned above, the process of the invention needs a catalytic system. This catalytic system is also an embodiment of the invention. By "catalytic system" is meant a mixture consisting of a metal complex and of a co-ingredient. The metal complex is used in substoichiometric, or catalytic amounts, relative to the starting aldehyde or ketone.

The metal complex has a general formula:

$$M(OR^8)_{4-n}X_n \qquad (VII)$$

wherein M is a tetravalent metal cation selected from the group consisting of Ti, Zr and Hf, $R^8$ represents a $C_{1-6}$ linear or branched alkyl group, X represents an halide such as a Cl or F atom, and the index n represents an integer from 1 to 3. Preferably, M represents Ti(IV) or Zr(IV), $R^8$ represents a linear or branched $C_{1-4}$ alkyl group, X represents a Cl atom and the index n represents 2 or 3.

The use of a mixture of metal complexes of formula (VII) is also convenient, especially if the catalyst is synthesized in situ, and without purification, prior to its use in the process.

The co-ingredient of the catalytic system is an alkyl or aromatic carboxylic acid anhydride containing 1 to 10 carbon atoms, $BF_3$ or an anhydrous salt selected from the group consisting of the sulfates, chlorides and bromides of a metal cation, said metal cation being selected from the group consisting of $Li^+$, $Na^+$, $K^+$, $Cs^+$, $Mg^{2+}$, $Ni^{2+}$, $Ca^{2+}$, $Zn^{2+}$, $Fe^{3+}$ and $Al^{3+}$. Preferably, the co-ingredient is selected from the group consisting of acetic, propionic or butyric anhydride, $BF_3$, the anhydrous $Na_2SO_4$ or $K_2SO_4$ and an anhydrous chloride or bromide of $Mg^{2+}$, $Fe^{3+}$ or $Zn^{2+}$.

The use of a mixture of two or three co-ingredients is also possible.

The process of the invention is advantageously performed in the presence of an excess, i.e., more that one molar equivalent, of starting ketone, relative to the starting aldehyde.

The metal complex can be added to the reaction medium in a large range of concentrations. As non-limiting examples, one can cite catalyst concentrations ranging from 0.001 to 0.20 molar equivalents, relative to the molar amount of the starting aldehyde (III) or (V). Preferably, the metal complex concentration will be comprised between 0.01 and 0.15 molar equivalents. It goes without saying that the optimum concentration of catalyst will depend on the nature of the latter and on the desired reaction time.

The co-ingredient can be added to the reaction medium in a large range of concentrations. As non-limiting examples, one can cite salt concentrations ranging from 0.05 to 1.2 molar equivalents, relative the number of moles of the starting aldehyde (III) or (V). Preferably, the salt concentration will be comprised between 0.15 and 1 molar equivalent. Yet, in another preferred embodiment the salt concentration will be comprised between 0.20 and 0.6 molar equivalents. It goes without saying that the optimum concentration of the additional agent will depend on the nature of the latter.

The process of the invention can be carried out in the presence or absence of solvent, but in any case it is advantageously performed in anhydrous conditions, wherein by "anhydrous" it is meant here a solvent which has a content in water below 1% by weight, preferably below 0.1%. When a solvent is required, it is possible to use a pure solvent or a mixture of solvents. The solvent must be chemically compatible with the reaction conditions, i.e. not interfere with the reaction, and not deactivate the catalyst, e.g. a weak or non-coordinating solvent. Preferred solvents for the process of the invention have a boiling point higher than 60° C. and are selected from the group consisting of ethers, esters, aromatic solvents, and linear or branched or cyclic hydrocarbons. More preferably, the solvent is toluene or an ether or ester with a boiling point higher than 80° C.

The temperature at which the process of the invention can be carried out is comprised between 60° C. and 140° C., preferably between 70° C. and 110° C. Of course a person skilled in the art is also able to select the reaction temperature as a function of the melting and boiling point of the starting and final products and/or the possible solvent.

EXAMPLES

The invention will now be described in further detail by way of the following examples, the temperatures are indicated in degrees centigrade (° C.); the NMR spectral data were recorded with a 360 MHz machine in $CDCl_3$, the chemical displacement δ are indicated in ppm with respect to the TMS as standard, the coupling constant J are expressed in Hz and all the abbreviations have the usual meaning in the art.

Example 1

Preparation of the Metal Catalyst Solution

A catalytic solution containing the $ZrCl_3(OPr)$ complex is obtained according to the procedure described in E. V. Vedejs et al., *J. Org. Chem.*, (1988), 53, 1593. The quantities were modified in order to obtain catalytic solution with a concentration of 1.2 mmole of metal per gram of catalytic solution.

A catalytic solution containing the $ZrCl_2(OPr)_2$ complex is obtained according to the procedure described in E. V. Vedejs et al., *J. Org. Chem.*, (1988), 53, 1593 but using an equimolar amount of $ZrCl_4$ and of $Zr(OPr)_4$. The quantities were modified in order to obtain catalytic solution with a concentration of 1.2 mmole of metal per gram of catalytic solution.

A catalytic solution containing the $TiCl_3(O^iPr)$ complex is obtained according to the procedure described in E. V. Vedejs et al., J. Org. Chem., (1988), 53, 1593 but using the $TiCl_4$ and the $Ti(O^iPr)_4$ complexes as starting materials. The quantities were modified in order to obtain catalytic solution with a concentration of 1.3 mmole of metal per gram of catalytic solution.

All the resulting solutions were used without further manipulation.

General procedure for preparing 1-(2,6,6-trimethyl-3-cyclohexen-1-yl)-2-buten-1-one

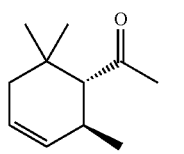

1-(2,6,6-trimethyl-3-cyclohexen-1-yl)-2-ethanone
Mw = 166

+

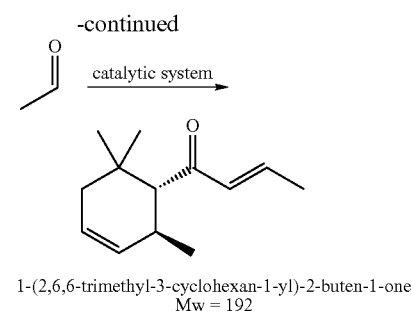

1-(2,6,6-trimethyl-3-cyclohexan-1-yl)-2-buten-1-one
Mw = 192

In a 250 ml flask were added 30 g (0.18 mole) of 1-(2,6,6-trimethyl-3-cyclohexen-1-yl)-2-ethanone (94% purity), 12.0 g of butyl acetate, an aliquot according to Table 1 of the catalytic solution as prepared above and a quantity of co-ingredient according to Table 1. The resulting mixture was stirred at 100° C. To said mixture, 4.0 g (0.09 mole) of acetaldehyde, diluted in 10 g of butyl acetate were introduced under the surface of the liquid, over 3 hours. After the completion of the introduction the reaction was cooled to 35° C. To the cooled reaction medium were added 10 g of acetic acid and then 40 ml of water. After stirring a few minutes, the water phase was removed and the organic phase was neutralized by washing it with 25 g of 20% aqueous potassium carbonate.

Finally, the butyl acetate was removed by distillation at 130–140° C. under ambient pressure and the crude product thus obtained was purified by distillation on a "Vigreux" column to recover the unreacted starting ketone and the final 1-(2,6,6-trimethyl-3-cyclohexen-1-yl)-2-buten-1-one. The product presented the analytical characteristics described in the literature (i.e. as in U.S. Pat. No. 4,211,242).

TABLE 1 reaction conditions and yields

| Run | Metal complex | Catalytic solution Aliquot | Co-ingredient | Co-ingredient quantities | Yields |
|---|---|---|---|---|---|
| 1 | $TiCl_3(O^iPr)$ | 3.46 g (0.05 m.e.) | $FeCl_3$ | 2.9 g (0.2 m.e.) | 14% |
| 2 | $TiCl_3(O^iPr)$ | 3.46 g (0.05 m.e.) | AcOAc | 9.18 g (1.0 m.e.) | 40% |
| 3 | $TiCl_3(O^iPr)$ | 3.46 g (0.05 m.e.) | $MgCl_2$ | 3.8 g (0.4 m.e.) | 22% |
| 4 | $TiCl_3(O^iPr)$ | 3.46 g (0.05 m.e.) | $BF_3$ | 1.28 g (0.1 m.e.) | 16% |
| 5 | $ZrCl_3(OPr)$ | 1.5 g (0.02 m.e.) | $MgCl_2$ | 3.8 g (0.4 m.e.) | 45% |
| 6 | $ZrCl_2(OPr)_2$ | 1.5 g (0.02 m.e.) | $MgCl_2$ | 3.8 g (0.4 m.e.) | 32% |

Notes to Table:
m.e.: molar equivalents relative to the acetaldehyde
AcOAc: acetic anhydride;
$O^iPr$: $OCH(CH_3)_2$;
OPr: $OCH_2CH_2CH_3$
Yields are based on the acetaldehyde.

Example 2

General Procedure for the Aldol Condensation Between Different Substrates

In a typical procedure, the co-ingredient and the catalyst (preparation and solution molarity: see Example 1) were charged in the flask containing the ketone and the solvent, then stirred vigorously and heated. The aldehyde (1 eq.) was added under the surface of the liquid over 3–5 hours (pure or in solution). Afterwards, the reaction mixture was cooled to 30° C. and diluted acetic acid was added (10% in water) under stirring. After 15 minutes, the water phase was removed and the organic phase neutralized by washing with diluted potassium carbonate (20% in water).

The organic product was concentrated under vacuum and the resulting crude product purified by distillation on a "Vigreux" column to recover the unreacted starting ketone and the corresponding product.

All the exact experimental conditions as well as the final yields of the product are summarized in Table 2. The product presented the analytical characteristics described in the literature.

TABLE 2 reaction conditions and yields

|   | Complex / Aliquot | Co-ingredient / Aliquot | T / ad.time | Solvent/ aliquot | Yields |
|---|---|---|---|---|---|
| 1 | TiCl$_3$(O$^i$Pr) 0.03 eq. | MgCl$_2$ 0.25 eq | 70° C. / 4 h | Butylacetate / 100% | 85% |
|   | TiCl$_3$(O$^i$Pr) 0.03 eq | AcOAc 1 eq | 70° C. / 4 h | Butylacetate / 100% | 44% |
| 2 | Complex / Aliquot | Co-ingredient Aliquot | T / ad.time | Solvent/ aliquot | Yields |
|   | ZrCl$_3$(OPr) 0.02 eq. | MgCl$_2$ 0.3 eq. | 100° C. / 5 h | Butylacetate / 100% | 71% (sum of isomers) |
| 3 | Complex / Aliquot | Co-ingredient / Aliquot | T / ad.time | Solvent/ aliquot | Yields |
|   | TiCl$_3$(O$^i$Pr) 0.03 eq. | MgCl$_2$ 0.3 eq. | 70° C. / 5 h | Butylacetate / 100% | 71% |
| 4 | Complex / Aliquot | Co-ingredient / Aliquot | T / ad.time | Solvent / aliquot | Yields |
|   | TiCl$_3$(O$^i$Pr) | MgCl$_2$ | 70° C. /  | — | 66% |
| 5 | Complex / Aliquot | Co-ingredient / Aliquot | T / ad.time | Solvent/ aliquot | Yields |
|   | TiCl$_3$(O$^i$Pr) 0.035 eq. | AcOAc 1 eq. | 70° C. 3 h | — | 72% |

Table Notes:
% w/w: percentage in weight
e.q. = e.q.: molar equivalent relative to the aldehyde
Complex / Aliquot = Metal complex / Catalytic solution Aliquot in e.q.
T / ad.time = Reaction temperature / aldehyde addition time
Solvent / aliquot = type of solvent / quantity, in weight % relative to the aldehyde
Yield is based on the aldehyde
For compound 2, the starting ketone is a mixture of at least two of 1-(2,6,6-trimethyl-1,3-cyclohexadien-1-yl)-1-ethanone, 1-(2,6,6-trimethyl-1,4-cyclohexadien-1-yl)-1-ethanone, 1-(2,6,6-trimethyl-2,4-cyclohexadien-1-yl)-1-ethanone, 1-(2,2-dimethyl-6-methylene-3-cyclohexen-1-yl)-1-ethanone and 1-(6,6-dimethyl-2-methylene-3-cyclohexen-1-yl)-1-ethanone.

What is claimed is:

1. A catalytic system consisting of a metal complex of formula $$M(OR^8)_{4-n}X_n \qquad (VII)$$

wherein M is a tetravalent metal cation selected from the group 4 of the periodic table, $R^8$ represents a $C_{1-6}$ linear or branched alkyl group, X represents an halide such as a Cl or F atom and the index n represents an integer from 1 to 3;

and of a co-ingredient which is an alkyl or aromatic carboxylic acid anhydride containing 1 to 10 carbon atoms, $BF_3$ or an anhydrous salt selected from the group consisting of the sulfates, chlorides and bromides of a metal cation, said metal cation being selected from the group consisting of Li$^+$, Na$^+$, K$^+$, Cs$^+$, Mg$^{2+}$, Ni$^{2+}$, Ca$^{2+}$, Zn$^{2+}$, Fe$^{3+}$ and Al$^{3+}$.

2. A catalytic system according to claim 1, wherein M represents Ti(IV) or Zr(IV), $R^8$ represents a $C_{1-6}$ linear or branched alkyl group, X represents a Cl or F atom and the index n represents an integer from 1 to 3;

and the metal cation of the co-ingredient is selected from the group consisting of Li$^+$, Na$^+$, K$^+$, Cs$^+$, Mg$^{2+}$, Ni$^{2+}$, Ca$^{2+}$, Zn$^{2+}$ and Fe$^{3+}$.

3. A catalytic system according to claim 1, wherein M represents Ti(IV) or Zr(IV), $R^8$ represents a linear or branched $C_{1-4}$ alkyl group, X represents a Cl atom and the index n represents 2 or 3.

4. A process according to claim 1, wherein the co-ingredient is selected from the group consisting of acetic, propionic or butyric anhydride, $BF_3$, the anhydrous $Na_2SO_4$ or $K_2SO_4$ and an anhydrous chloride or bromide of $Mg^{2+}$, $Fe^{3+}$ or $Zn^{2+}$.

* * * * *